US00PP16765P3

(12) United States Plant Patent

Lintott

(10) Patent No.: US PP16,765 P3

(45) Date of Patent: Jul. 4, 2006

(54) ***CHRYSANTHEMUM* PLANT NAMED 'LILAC TENSION'**

(50) Latin Name: *Chrysanthemum morifolium*
Varietal Denomination: Lilac Tension

(75) Inventor: Keith G. Lintott, Bognor Regis (GB)

(73) Assignee: Cleangro, Ltd, Chichester (GB)

( * ) Notice: Subject to any disclaimer, the term of this patent is extended or adjusted under 35 U.S.C. 154(b) by 41 days.

(21) Appl. No.: 11/055,217

(22) Filed: Feb. 9, 2005

(65) Prior Publication Data

US 2005/0177914 P1 Aug. 11, 2005

(51) Int. Cl.
*A01H 5/00* (2006.01)

(52) U.S. Cl. ..... Plt./297

(58) Field of Classification Search ..... Plt./297, Plt./292

See application file for complete search history.

(56) References Cited

PUBLICATIONS

1998 Ficor catalog, listing the variety 'Biarritz'. See, e.g., pp. 4 and 7.

1999 Ficor catalog, listing the variety 'Biarritz'. See, e.g., pp. 4 and 7.

2000 Ficor catalog, listing the varieties 'Biarritz' and 'Tension'. See, e.g., pp. 4 and 7.

2001 Ficor catalog, listing the varieties 'Biarritz' and 'Tension'. See, e.g., pp. 4 and 12.

2002 Ficor catalog, listing the varieties 'Biarritz' and 'Tension'. See, e.g., pp. 4 and 12.

2003 Ficor catalog, listing the varieties 'Biarritz' and 'Tension'. See, e.g., pp. 2 and 10. See also the photograph of 'Tension' in the inside back cover.

2004 Ficor catalog, listing the varieties 'Biarritz', 'Tension' and 'Lilac Tension', at pp. 2 and 10. See also the photograph of Lilac Tension in the inside front cover. 2004 catalog first publicly distributed on or after Oct. 1, 2003, outside the United States.

2003 Cleangro brochure listing the variety 'Tension', See, p. 2 (photograph).

2004 Cleangro brochure listing the variety 'Tension'. See, p. 4 (photograph).

2003 Royal Van Zanten Catalog listing the variety 'Tension'. See p. 53 (photograph), 55 and 59.

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *Chrysanthemum* plant named 'Lilac Tension' having a flat capitulum of bright lilac spoon petalled single type flowers.

1 Drawing Sheet

Latin name of the genus and species: Botanical classification: *Chrysanthemum morifolium.*

Variety denomination: The new *Chrysanthemum* variety denomination is 'Lilac Tension.'

BACKGROUND OF THE INVENTION

The present invention comprises a new and distinct cultivar of *Chrysanthemum* botanically known as *Chrysanthemum morifolium,* and referred to by the variety name 'Lilac Tension.'

'Lilac Tension,' identified as 11015-17, was found in a naturally occurring whole plant mutation grown in a controlled planting of the variety 'Tension' in Chichester, West Sussex, United Kingdom.

The new variety 'Lilac Tension' has been asexually reproduced by vegetative cuttings in Chichester, West Sussex, United Kingdom and the distinguishing characteristics are retained through successive generations of asexual reproduction.

BRIEF SUMMARY OF THE INVENTION

'Lilac Tension' is a cut type of *Chrysanthemum* plant variety having a strong upright habit and a flat capitulum of single type flowers and spoon shaped ray florets.

Comparison with Parent

Plants of the new *Chrysanthemum* variety 'Lilac Tension' are similar to the parent variety 'Tension' in plant habit and growth rate. However, in side-by-side comparisons in Chichester, West Sussex, United Kingdom, under commercial practice, plants of the new *Chrysanthemum* variety 'Lilac Tension' differed from plants of the parent variety 'Tension' in the following characteristics.

1. The new *Chrysanthemum* variety 'Lilac Tension' produces lilac colored spoon petalled single flowers whereas the parent variety 'Tension' produces purple colored spoon petalled single flowers.
2. Plants of the new *Chrysanthemum* variety 'Lilac Tension' have larger flowers than plants of the variety 'Tension.'
3. Plants of the new *Chrysanthemum* variety 'Lilac Tension' are more vigorous than plants of the variety 'Tension.'

Comparison with Other Varieties

Plants of the *Chrysanthemum* variety 'Lilac Tension' are similar to the variety 'Biarritz' in plant habit and growth rate.

However, in side-by-side comparisons in Chichester, West Sussex, United Kingdom, under commercial practice, plants of the new *Chrysanthemum* variety 'Lilac Tension' differed from plants of the variety 'Biarritz' in the following characteristics.

1. The new *Chrysanthemum* variety 'Lilac Tension' produces lilac colored spoon petalled single flowers whereas the variety 'Biarritz' produces purple colored quilled petalled single flowers.
2. Plants of the new variety 'Lilac Tension' have larger and longer inflorescence than plants of the variety 'Biarritz.'

BRIEF DESCRIPTION OF ILLUSTRATION

Typical specimens of the plant and flowers for the new *Chrysanthemum* variety 'Lilac Tension' are shown in the accompanying digital photograph. The colors shown are as true as possible within the usual limits of this kind of illustration.

FIG. 1 is a whole plant view of the new *Chrysanthemum* variety 'Lilac Tension' grown as a cut flower. The plant shown in the illustration is 49 days old from the commencement of Short Days.

DETAILED BOTANICAL DESCRIPTION

The following description of the new *Chrysanthemum* variety 'Lilac Tension' is of plants grown in a greenhouse in Chichester, West Sussex, United Kingdom in the month of July. The variety has not been observed under all possible environmental conditions. The phenotype may vary significantly with variations in the environment such as temperature, length of day and light intensity, without any variance in genotype. The commercial classification of the new variety is a cut flower *chrysanthemum*.

Plants of the new variety have been grown successfully under temperature conditions averaging about 18° C. at night and about 18° C. to 24° C. during the day under light conditions of about 5000 to 6000 foot candles. The plants respond well to the use of growth retardant, such as one B9 treatment at about 2 gram/liter. To produce a commercial product the plants should not be pinched and the center bud has to be removed 4 weeks before flowering. It has been observed that the shelf life of the new variety is about 18 days with a response time of about 7 weeks. The new variety is suitable for growth in a temperature range of 18° C. to 24° C.

The new variety may be produced as a spray *Chrysanthemum*. The following description is with respect to a plant produced as a cut *Chrysanthemum*. In the description of this new *Chrysanthemum* variety, color values have been taken from The Royal Horticultural Society Colour Chart (R.H.S.C.C.).

PLANT

Plant Type: Single type cut *Chrysanthemum*.
Habit: Upright.
Height: 75 cm–85 cm.
Width: 15 cm–20 cm.
Stem Color: 146 C.
Response Time: 7 weeks.
Vigor: Moderate.
Shelf Life: Near 18 days.
Disease (Susceptibility/Resistance observed): None observed to date.
Pest (Susceptibility/Resistance observed): None observed to date.
Drought and temperature (Susceptibility/Resistance observed): None observed to date.
Growth retardant type and treatment: 1 application B9 after 2 weeks in Short Days of 2 gram/litre.
The plants were grown for 2 weeks in Long Day conditions (20 hours of light) and then transferred to Short Day conditions (13 hours of dark).
Propagation:
*Type.*—Vegetative Propagation via Stem cuttings.
*Time to rooting.*—14 days with soil temperatures of 22° C.
*Rooting habit.*—Fine, Fibrous and Well Branched.

FOLIAGE

Compound or single: Single.
Arrangement of leaves: Alternate.
*Shape of leaf.*—Typical 4 lobed.
*Size of leaf.*—Width.—5.5 cm–7.5 cm. Length.—8 cm–13 cm.
*Leaf/Apex.*—Mucronate.
*Base.*—Acute.
*Attachment.*—Petioled.
*Aspect.*—Slightly undulating.
*Margin.*—Palmately lobed.
*Surface characteristics.*—Top.—Slightly Pubescent.
Bottom.—Slightly Pubescent.
Petiole:
*Color.*—137A.
*Length.*—1.5 cm–2 cm.
Venation: Net. Mid vein prominent at underside.
*Color.—Upper side.*—near 139C.
*Under side.*—near 139C.
Color:
*Mature Leaf,* upper side.—Near 138A; under side.—near 138B.
*Young Leaf,* upper side.—Near 139A; under side.—near 139B.

FLOWER

Flower appearance: Matte.
Flower type: Single.
Flower form: Slightly cupped.
Flower shape: Round.
Flowering habit: Upright.
Number of blossoms per branch: 1–4.
Inflorescence form: Corymbiform.
*Depth of fully expanded blossoms.*—1.5 cm–2 cm.
*Diameter of fully expanded blossoms.*—3.5 cm–4.5 cm.
Phyllaries:
*Number.*—16–20.
*Color.*—Near 137A.
*Length.*—0.5–0.8 cm.
*Width.*—0.2–0.4 cm.
*Texture/Appearance.*—Slightly Shiny and Slightly Pubescent.
Pedicel:
*Length.*—7–18 cm.
*Diameter.*—0.3 cm–0.5 cm.
*Angle from stem.*—20°–25°.
*Color.*—near 137B.
*Surface.*—Slightly pubescent.
*Habit.*—Slightly curved.
*Strength.*—Medium.

Ray florets:
*Form/Shape.*—Spatulate.
*Texture/Appearance.*—Dull Smooth.
*Number per flower.*—55–70.
*Length.*—1.0–2.5 cm; *Width.*—0.2–0.8 cm.
*Apex.*—Rounded.
*Base.*—Tubular.
*Margin.*—Entire.
Disc florets:
*Form/Shape.*—Tubular.
*Texture/Appearance.*—Dull Smooth.
*Number per flower.*—5–7.
*Length.*—0.5–0.8 cm; *Width.*—0.1 cm.
*Diameter of disc.*—0.4–0.6 cm.
Fragrance: None observed.
Flower Bud (at onset of color):
*Length.*—0.7–1.0 cm.
*Diameter.*—0.6–0.9 cm.
*Form/Shape.*—Globular.
General flower color:
1. *Ray florets,* upper side.—Immature.—near 69C blade—71C tubular base. Mature.—near 69C blade—71C tubular base. Older/Fading.—near 69C blade—71C tubular base.
2. *Ray florets,* under side.—Immature.—near 71C. Mature.—near 71C. Older/Fading.—near 71C.
3. *Disc florets.— Immature.—near* 71C. Mature.—near 71C. Older/Fading.—near 71C.
4. *Bud.*—near 139C.

Flower progression with age; Color fades very slightly with age.
The lastingness of bloom is about 18 days.

REPRODUCTIVE ORGANS

Gynoecium present on Ray florets only.
Ray florets per individual flower:
*Pistil number.*—20–35 observed.
*Stigma color.*—near 151B.
*Stigma shape.*—Forked.
*Style color.*—near 151B.
*Style length.*—0.1 cm–0.2 cm.
Androecium present on Disc florets only.
Disc florets per individual flower:
*Stamen number.*—10–15 observed.
*Anther shape.*—Club shaped.
*Anther color.*—near 14A.
*Pollen/Color.*—near 17B.
*Pollen quantity.*—Small.
Fruit and Seeds: None observed.

What is claimed is:

1. A new and distinct variety of *Chrysanthemum* plant, substantially as described and illustrated herein.

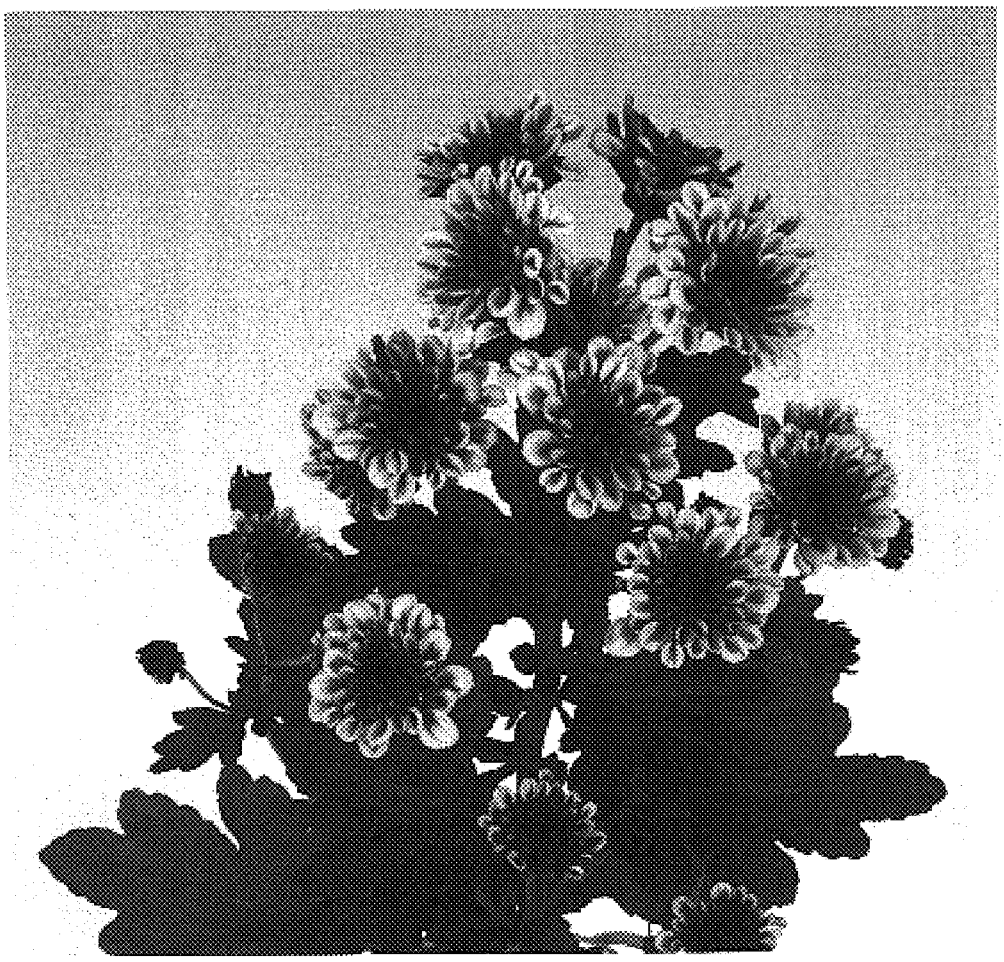

* * * * *